United States Patent
Kauppi et al.

(10) Patent No.: US 9,512,949 B2
(45) Date of Patent: Dec. 6, 2016

(54) CONNECTOR PART AND FLUID CONNECTION STRUCTURE

(75) Inventors: Jani Kauppi, Helsinki (FI); Heikki Haveri, Helsinki (FI)

(73) Assignee: CAREFUSION CORPORATION, San Diego, CA (US)

(*) Notice: Subject to any disclaimer, the term of this patent is extended or adjusted under 35 U.S.C. 154(b) by 0 days.

(21) Appl. No.: 13/329,993

(22) Filed: Dec. 19, 2011

(65) Prior Publication Data

US 2012/0153613 A1  Jun. 21, 2012

(30) Foreign Application Priority Data

Dec. 21, 2010 (EP) .................................... 10196144

(51) Int. Cl.
| | |
|---|---|
| *F16L 47/16* | (2006.01) |
| *A61M 16/08* | (2006.01) |
| *A61M 39/10* | (2006.01) |
| *F16L 47/06* | (2006.01) |
| *F16L 47/08* | (2006.01) |

(52) U.S. Cl.
CPC .............. *F16L 47/16* (2013.01); *A61M 16/085* (2014.02); *A61M 16/0816* (2013.01); *A61M 39/10* (2013.01); *A61M 39/1011* (2013.01); *F16L 47/06* (2013.01); *F16L 47/08* (2013.01)

(58) Field of Classification Search
CPC ............ F16L 47/08; F16L 47/16; F16L 47/06; F16L 47/065
USPC ......... 285/355, 374, 921, 338, 347; 604/905
See application file for complete search history.

(56) References Cited

U.S. PATENT DOCUMENTS

| | | | | |
|---|---|---|---|---|
| 115,917 | A * | 6/1871 | Wharton ....................... | 285/921 |
| 1,216,609 | A * | 2/1917 | Robinson ..................... | 285/347 |
| 2,314,386 | A * | 3/1943 | Brend ........................... | 285/347 |
| 2,542,701 | A * | 2/1951 | Press ............................ | 285/281 |
| 2,982,569 | A * | 5/1961 | Miller ................... | F16L 13/113 |
| | | | | 285/230 |
| 3,233,925 | A | 2/1966 | Stevens | |
| 3,258,279 | A * | 6/1966 | Johnsen ....................... | 285/110 |
| 3,315,970 | A * | 4/1967 | Holoway ..................... | 285/345 |
| 3,390,890 | A * | 7/1968 | Kurtz ............................ | 285/231 |
| 3,394,954 | A * | 7/1968 | Sarns ............................ | 285/319 |
| 3,482,859 | A * | 12/1969 | Bowlin ........................ | 285/347 |

(Continued)

FOREIGN PATENT DOCUMENTS

| | | | |
|---|---|---|---|
| CH | 404 314 | | 12/1965 |
| EP | 0030062 | * | 6/1981 |

(Continued)

OTHER PUBLICATIONS

European Office Action in EP Application No. 10196144.9 dated Jan. 12, 2015, 5 pages.

(Continued)

*Primary Examiner* — David E Bochna
(74) *Attorney, Agent, or Firm* — McDermott Will & Emery LLP

(57) ABSTRACT

Connector part comprising a body part for connecting to a counterpart for creating a fluid tight seal when fitted together. The connector part also comprises a seal element made of resilient material and a space which is capable to receive the seal element made of resilient material when the fluid tight seal is made. The connector part can be used for forming a fluid tight connection structure.

20 Claims, 1 Drawing Sheet

(56) References Cited

U.S. PATENT DOCUMENTS

| | | | | |
|---|---|---|---|---|
| 3,635,499 | A * | 1/1972 | Reddy | 285/111 |
| 3,792,878 | A * | 2/1974 | Freeman | 285/347 |
| 3,986,508 | A * | 10/1976 | Barrington | 604/905 |
| 4,018,461 | A * | 4/1977 | Bram | 285/110 |
| 4,084,827 | A | 4/1978 | Wolf | |
| 4,174,125 | A * | 11/1979 | Wyss | 285/369 |
| 4,187,846 | A * | 2/1980 | Lolachi et al. | 604/905 |
| 4,258,935 | A * | 3/1981 | Rodrigo et al. | 285/423 |
| 4,298,206 | A * | 11/1981 | Kojima | 285/110 |
| 4,334,551 | A * | 6/1982 | Pfister | 604/905 |
| 4,346,703 | A * | 8/1982 | Dennehey et al. | 604/905 |
| 4,354,490 | A * | 10/1982 | Rogers | 604/905 |
| 4,572,523 | A * | 2/1986 | Guettouche et al. | 285/231 |
| 4,583,771 | A * | 4/1986 | Wasterberg | 285/347 |
| 4,588,402 | A * | 5/1986 | Igari et al. | 604/905 |
| 4,690,414 | A * | 9/1987 | Haaland | 285/345 |
| 4,735,440 | A * | 4/1988 | Sauer | 285/347 |
| 4,906,010 | A * | 3/1990 | Pickering et al. | 285/231 |
| 4,941,689 | A * | 7/1990 | Sjoberg | 285/921 |
| 5,123,677 | A * | 6/1992 | Kreczko et al. | 285/921 |
| 5,143,381 | A * | 9/1992 | Temple | F16L 21/035 285/94 |
| 5,324,083 | A * | 6/1994 | Vogelsang | 285/345 |
| 5,518,279 | A * | 5/1996 | Harle | 285/349 |
| 5,549,583 | A * | 8/1996 | Sanford et al. | 604/905 |
| 5,687,997 | A * | 11/1997 | Beacom | 285/379 |
| 6,171,287 | B1 * | 1/2001 | Lynn et al. | 604/905 |
| 6,293,556 | B1 * | 9/2001 | Krausz | 285/369 |
| 6,423,053 | B1 * | 7/2002 | Lee | 604/905 |
| 6,569,125 | B2 * | 5/2003 | Jepson et al. | 604/905 |
| 6,595,964 | B2 * | 7/2003 | Finley et al. | 604/905 |
| 7,156,424 | B2 * | 1/2007 | McCord | 285/92 |
| 8,454,579 | B2 * | 6/2013 | Fangrow, Jr. | 604/539 |
| 8,568,371 | B2 * | 10/2013 | Siopes et al. | 604/256 |
| 2003/0098430 | A1 * | 5/2003 | Leinsing et al. | 251/149.6 |
| 2005/0082828 | A1 * | 4/2005 | Wicks et al. | 285/921 |
| 2008/0190485 | A1 * | 8/2008 | Guala | 137/1 |

FOREIGN PATENT DOCUMENTS

| | | |
|---|---|---|
| EP | 2138202 A1 | 12/2009 |
| FR | 2522969 A1 | 9/1983 |

OTHER PUBLICATIONS

European Office Action for Application No. 10196144.9, dated Oct. 27, 2015, 4 pages.

European Office Action for Application No. 10196144.9, dated May 2, 2016, 3 pages.

\* cited by examiner

CONNECTOR PART AND FLUID CONNECTION STRUCTURE

BACKGROUND OF THE INVENTION

The disclosure relates to connector part comprising a body part for connecting to a counterpart for creating a fluid tight seal when fitted together. The disclosure relates further to fluid connection structure using the connector part.

As described above the disclosure relates generally to a fluid connection for reducing a fluid volume and making a secure seal in said connection. Especially the disclosure describes the fluid connection to reduce an extra fluid volume when using connectors made using multi shot injection molded parts. The disclosure relates also to sample tubing connections used in analyzing equipment such as gas analyzing equipment for patient respiratory gas.

In anesthesia or in intensive care, the condition of a patient is often monitored e.g. by analyzing the air exhaled by the patient for its carbon dioxide content. For this reason a small portion of the respiratory gas is delivered to a gas analyzer. The sample is carried along a sampling tube connected in one end often to a respiratory tube adapter and the other end to the gas analyzer. This sampling tube is typically disposable and must have some kind of reliable and tight but simple and cheap connectors.

Almost all pneumatic connectors in the respiratory system used earlier in the field have tapered conical contact surfaces. Such connectors are simple, easy to connect and cheap to make and they still provide an airtight and reliable connection. The connection such as a well-known fitting called Luer-Lok, a registered trademark of Becton Dickinson of Franklin Lakes, N.J. USA, has been in general use for gas sampling but also other similar connectors with differing dimensions can be used.

The tapered portion of the connector is normally conical with straight cross section sides because it gives a reliable and tight connection using a large contact area. The tapered portion could in principle also have curved cross section sides or one tapered connector in combination with a suitably designed semi-rigid counterpart. The contact surface responsible for the tightness is always on the tapered portion of the connector.

A gas analyzer designed to measure respiratory gas in real time has to be fast enough to resolve changes in the gas content. This is especially true for carbon dioxide, which varies from close to zero in the inspiratory phase to about 5% in the expiratory phase of the breathing cycle. It is then very important to streamline the complete gas sampling system. Many portions of the system with slowed down response can easily add up to unacceptable performance of the gas analyzer.

The reason for an increased rise time of e.g. carbon dioxide is often an extra fluid volume, a dead space in the pneumatic line, where the gas flow is slowed down. The tapered conical connector is susceptible to such dead space, especially if the inner dimensions are significantly larger than those of the bore or sampling line itself. The inherent construction of the conical connector is such that dead space always is introduced and the amount is critically dependent on the tolerance of the conical dimensions. The connectors must allow for axial or longitudinal play in order to avoid the situation of touching axially because then air leak is likely to occur. Therefore, the tolerances always define an axial extra fluid volume in the connection to ensure tightness at the conical surfaces.

Minimal dead space is essential also in gas or liquid chromatography. An attempt to make connections with capillaries is described for example in U.S. Pat. No. 6,969,095 B2. The female part of the connection is slightly tapered in order to accept the cylindrical capillary tube and make a tight press-fit. This connector fitting is specially designed for conditions encountered in liquid or gas chromatography and is not intended for repeatedly made reliable connections like in gas analyzers. Robustness inevitably adds dead space to the bore of the connection.

In neonatal main ventilation circuits, extra fluid volume has to be as small as possible. There are different solutions to this problem. The connections are also conically tapered even if the dimensions are much larger than what would be used for a gas sampling system. In one solution there is a sliding internal passage filling the dead space and in another solution a compressible member is used to exclude the extra fluid volume.

With the current Luer-Lok type design it is impossible to know if the connector is connected leak-proof. The connectors can wedge together so that the connection seems to be tight but it is in fact leaking. Gas sampling done by suction created by a pump can dilute if there is a leak in the sampling line. Ventilator pressure changes will also influence the gas sampling if there is a leak in the sampling line.

BRIEF DESCRIPTION OF THE INVENTION

The above-mentioned shortcomings, disadvantages and problems are addressed herein which will be understood by reading and understanding the following specification.

One embodiment of the connector part comprises a body part for connecting to a counterpart for creating a fluid tight seal when fitted together. The embodiment is characterized in that the connector part also comprises a seal element made of resilient material and a space which is capable to receive the seal element made of resilient material when the fluid tight seal is made.

The embodiment described above can be materialized by making the body part as a female part or a male part.

In yet another embodiment fluid connection structure is created in which a connector part described above is used.

DETAILED DESCRIPTION OF THE INVENTION

Figure 1:
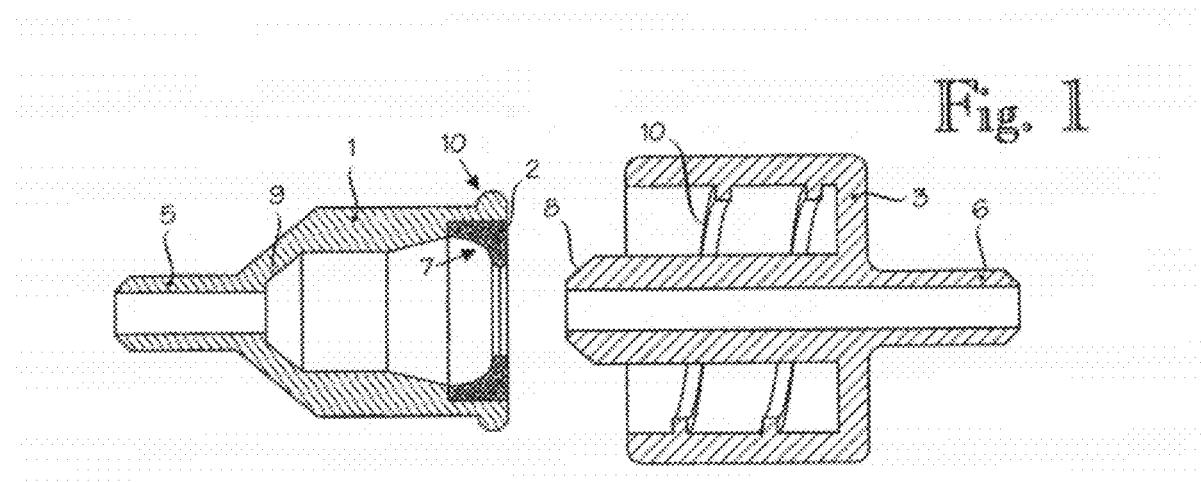
FIG. 1 shows one embodiment before actual connecting step.
Figure 2:
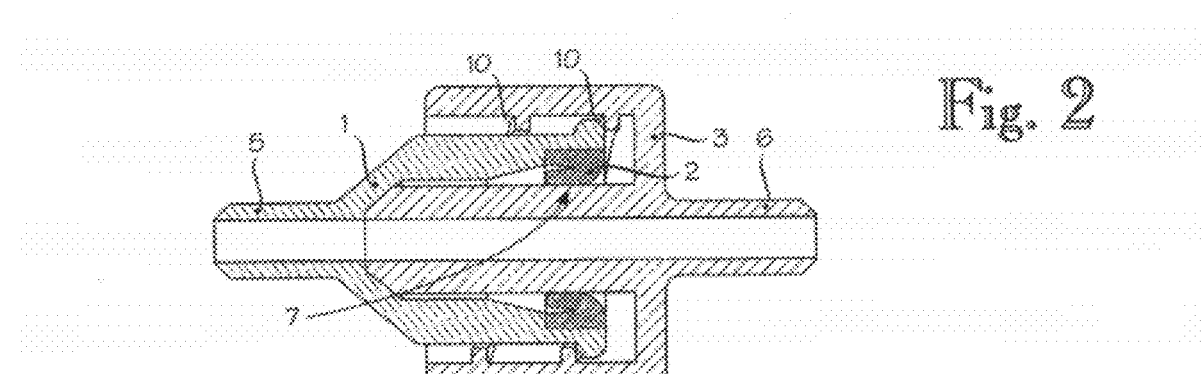
FIG. 2 shows the embodiment of FIG. 1 after the connection step has been carried out and FIG. 3 shows another embodiment before actual connecting step.

FIGS. 1 and 2 show the first embodiment. The embodiment of FIGS. 1 and 2 comprises a body part 1 having a rigid or semi-rigid structure. The body part 1 comprises further a seal element for creating a fluid tight seal with a counterpart to be fitted to the body part. The term fluid refers here for example to gases or liquids.

The seal element 2 is made of resilient material. The term resilient material means here that the seal element 2 is made of material which is more resilient than the material of the body part 1. The body part 1 is a rigid or semi rigid structure. Said resilient material can be for example soft material.

In the embodiment of FIGS. 1 and 2 the body part 1 is a female part. FIGS. 1 and 2 show with reference 3 a counterpart which in this embodiment is a male part. The counterpart 3 is a rigid or semi-rigid structure. Both the body part 1 and the counterpart 3 can be for example cylindrical structures. The resilient seal element 2 acts as the primary seal, sealing the connection when the seal encircles the counterpart 3. The embodiment shown uses male and female parts.

The structure shown in FIGS. 1 and 2 form a fluid connection. Said fluid connection may be for example a sampling tube connected in one end to a respiratory tube and the other end to the gas analyzer. As told earlier said sampling tube is typically disposable and must have some kind of reliable and tight and also cheap connector structures. The sampling tube may be attached to a first stud 5 of the body part and the counterpart 3 may be connected via a second stud 6 and connecting pipe to the breathing tube of a patient.

The matters relating to the fluid connection discussed above are familiar matters to a person skilled in the art, and therefore said matters are not discussed in detail here.

As discussed before the extra fluid volume, i.e. the dead space in the pneumatic line leads to slow down of the fluid flow which in turn leads to unacceptable performance of the gas analyzer. The idea in the embodiments shown is to reduce, i.e. to minimize said extra or dead fluid volume. Said idea is materialized so that the sealing assembly comprises a seal element 2 made of resilient material and further a space 7. The space 7 is capable to receive the seal element 2 made of resilient material when the fluid tight seal is made. FIG. 2 shows clearly that when bent or deformed the resilient seal element 2 fills the dead space and therefore minimizes the volume of the dead space. Space 7 is located behind the seal element 2 when seen in the join direction so that the seal element 2 can for example bend into the space 7 when the connection is made.

As discussed above the space 7, e.g. a cavity in the body part 1, which allows the resilient seal element 2 to for example bend or deform when the second connector is inserted. The volume of the space 7 is preferably as big as the volume of the deformed resilient seal element 2 or bigger. It can also be smaller than the deformed seal. In this case the insertion of the connection requires more force, but can be done. However, the seal might be damaged.

Resilient seal element 2 may be located at the tip portion of the body part 1 as shown in FIGS. 1 and 2. In the embodiment shown the seal element 2 has a circular shape. In the embodiment shown the seal element 2 is placed on the inner wall of the body part 1. The seal element 2 has a thin wall, which enables it to deform and/or bend when the male connector is inserted. The situation in which the counterpart 3, i.e. the male part in the embodiment of FIGS. 1 and 2 is shown in FIG. 2.

The seal element may also be placed to partly or completely on the outer circular front surface of the body part 1 so that when connected the seal element may bend in the way as shown in FIG. 2.

In the embodiment of FIGS. 1 and 2 the space 7 is placed adjacent to the seal element.

The body part 1 and the counterpart 3 forming the fluid connection structure may also have conical structure formed by conical sealing surfaces 8 and 9. Said conical structure makes the body part and the counterpart concentric and the flow fluent. Said conical structure feature can also act as a secondary seal structure if the connector parts are locked for example using appropriate elements 10 enabling to create tightening force. Said elements 10 may comprise a thread or snap fixture elements, forcing the sealing surfaces 8, 9 together to form said secondary seal. Said sealing surfaces however can also be flat surfaces.

Said secondary seal does not have to be leak-proof. It acts as a barrier between the flow channel and the inner space 7 of the connection. The conical features can be on both connectors or they can be on either connector, while the mating surface of the opposite connector remains for example flat. Both secondary sealing surfaces can also be flat. It is also quite possible to make an embodiment in which the only seal is the primary seal.

With the embodiment described above it is easy to minimize the dead space in the connection bore since the sealing surfaces are allowed to touch axially, while still remaining airtight.

The body part 1 can be made using two shot injection molding. The mold core that forms the negative draft cavity will be removed in the second phase utilizing the elasticity of the soft seal material. Two shot injection molding makes it feasible to manufacture the otherwise complex design in the required numbers.

The two shot injection molding technique described above is however the only possibility to materialize the embodiments described. The body part 1 can also be manufactured by using two separate injection molding machines. First phase (rigid part) is injected first and will be transferred from the first mold into the second. It will act as an insert, when the resilient material is injected.

Figure 3:
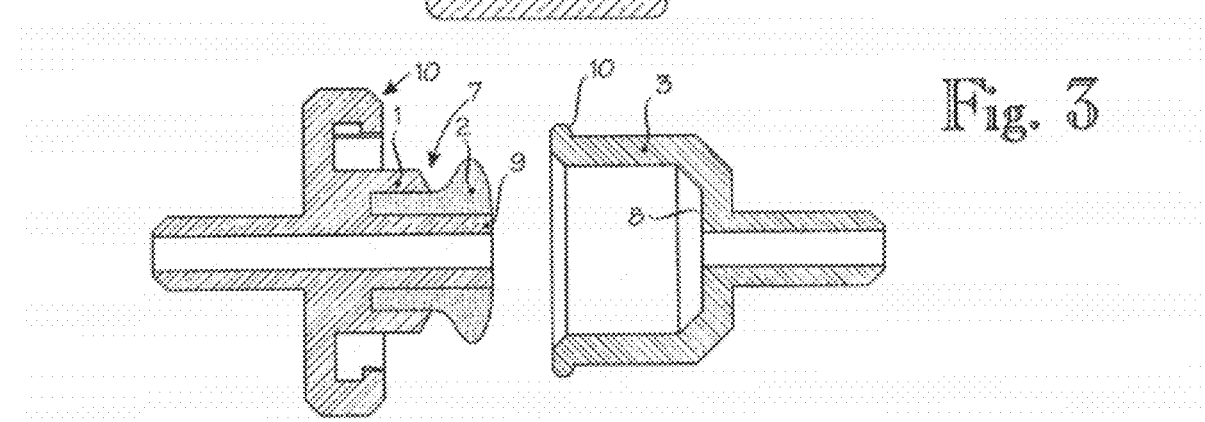
Figure 4:
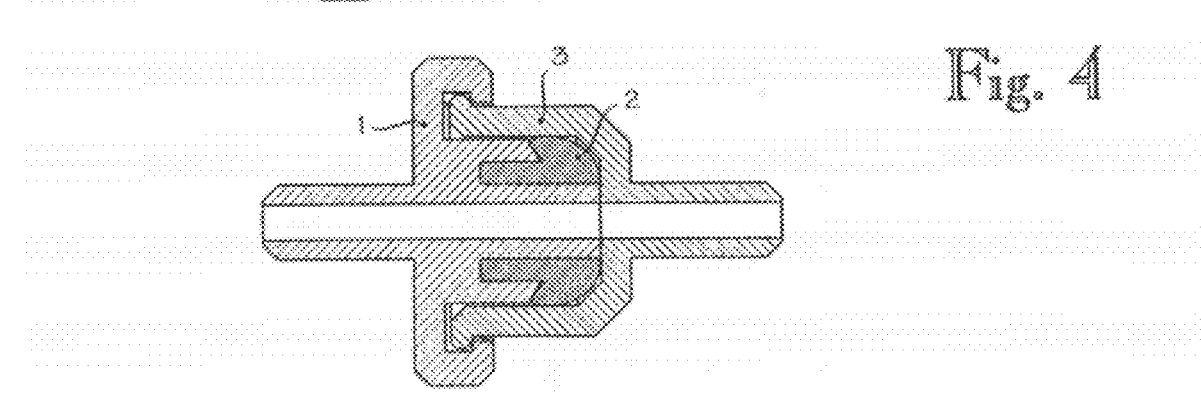
FIG. 4 shows the embodiment of FIG. 3 after the connection step has been carried out.

FIGS. 1 and 2 show an embodiment in which the body part 1 is a female part acting together with a male part acting as a counterpart 3. This is however not the only possibility. FIGS. 3 and 4 show schematically an embodiment in which the body part 1 is a male part acting together with a female part acting as a counterpart 3. FIGS. 3 and 4 use the same reference numbers in corresponding details as used in FIGS. 1 and 2.

The embodiment shown in FIGS. 3 and 4 can be manufactured in the same way as described above in connection with the embodiment of FIGS. 1 and 2, i.e. by using for example two shot injection molding or two separate injection moldings.

In the embodiment of FIGS. 3 and 4 the secondary sealing is formed by flat sealing surfaces 8, 9. It is also quite possible also in this embodiment to use conical surfaces for creating the secondary sealing. In the embodiment shown in FIGS. 3 and 4 the seal element 2 is placed on the surface of the body part 1, i.e. on the surface of the male part. In the embodiment of FIGS. 3 and 4 the elements 10 creating tightening force are snap connector elements.

The written description uses examples to disclose the invention, including its best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A connector part, comprising:
   a seal element made of a resilient material, the seal element comprising a body portion extending axially and a flange portion extending radially from the body portion at a first end of the body portion; and
   a body part configured to connect to a counterpart to create a fluid tight seal when fitted together, the body part comprising a space defining a first portion configured to receive the body portion of the seal element and a dead space portion defining a volume adjacent the first portion, the body part comprising an outer tip portion having a flat outer surface, the body part defining an opening, the first end of the body portion adjacent to the outer tip portion, a portion of the body part near a second end of the seal element comprising a slanted surface directly connected to a parallel surface parallel with an outer wall of the body part;
   wherein the flange portion of the seal element is positioned at the outer tip portion and has a substantially flat outer surface forming a substantially continuous surface with the outer tip portion, the flange portion configured to bend towards the body portion and into the dead space portion to substantially fill the volume of the dead space portion when the fluid tight seal is made;
   wherein the seal element is positioned radially around the opening such that the opening is open; and
   wherein the body part further comprises a sealing surface which provides a secondary seal surface, the sealing surface separate from the slanted surface and the parallel surface.

2. The connector part of claim 1, wherein the body part is a female part.

3. The connector part of claim 2, wherein the seal element is an annular element made of resilient material and placed on an inner wall of the female part, and the space is an annular space positioned adjacent the seal element.

4. The connector part of claim 3, wherein the volume of the space is the same as or bigger than the volume of the seal element in a deformed state.

5. The connector part of claim 3, wherein the volume of the space is smaller than the volume of the seal element in a deformed state.

6. The connector part of claim 2, wherein the sealing surface is a flat surface or a conical surface.

7. The connector part of claim 1, wherein the sealing surface is a conical surface or a flat surface.

8. The connector part of claim 1, wherein the body part is a male part.

9. The connector part of claim 8, wherein the seal element is an annular element placed on a wall of the male part, and the space is an annular space adjacent to the seal element.

10. The connector part of claim 8, wherein the volume of the space is the same as, bigger than, or smaller than the volume of the seal element in a deformed state.

11. The connector part of claim 1, wherein the body part is provided with elements that enable a tightening force to be applied to the body part.

12. The connector part of claim 11, wherein the elements that enable the tightening force to be applied to the body part comprise a spiral part.

13. A female connector part, comprising:
   a female body part configured to connect to a male counterpart to create a fluid tight seal when fitted together, the female body part having an inner wall, an outer tip portion having an outer front surface, and a dead space volume near the inner wall, the inner wall defining a cavity; and
   a seal element made of a resilient material and located along the inner wall such that the cavity is open, the seal element comprising a body portion extending axially along the inner wall and a flange portion extending radially into the cavity from the body portion at a first end of the body portion, the first end of the body portion adjacent the outer tip portion, the flange portion having a substantially flat outer surface and is continuous with the outer front surface to form a substantially flat and continuous surface, and the flange portion configured to bend into the dead space volume to substantially fill the dead space volume when the fluid tight seal is made;
   wherein a portion of the inner wall immediately adjacent a second end of the seal element comprises a slanted surface slanting inwards from the second end and towards the cavity and directly connected to a parallel surface parallel to an outer wall of the female body part, and the parallel surface is directly connected to a sealing surface separate from the slanted surface, and wherein the slanted surface, the parallel surface, and the sealing surface define the inner wall.

14. The female connector part of claim 13, wherein the female body part includes a thread element defining the outer front surface and extending away from the seal element.

15. The female connector part of claim 13, wherein the female body part is a rigid or semi-rigid structure.

16. The female connector part of claim 13, wherein the sealing surface comprises a flat or conical surface which provides a secondary seal surface.

17. A male connector part, comprising:
   a male body part configured to connect to a female counterpart to create a fluid tight seal when fitted together, the male body part having an outer wall, a male tip defining an outer front surface and a cavity, and a dead space volume near the outer wall; and
   a seal element made of a resilient material and located along the outer wall adjacent the male tip such that the cavity is open, the seal element comprising a body portion extending axially along the outer wall and a flange portion extending radially from the body away from the male tip, the flange portion having a substantially flat outer surface and is continuous with the outer front surface to form a substantially flat, continuous surface, and the flange portion is configured to bend into the dead space volume to substantially fill the dead space volume when the fluid tight seal is made;
   wherein a portion of the male body part near a second end of the seal element and adjacent the dead space volume comprises a slanted surface slanting outwards from the seal element and away from the first end of the seal element and connected to a parallel surface parallel to an outer wall of the male body part.

18. The male connector part of claim 17, wherein the male body part includes a snap fixture element defining an opening that expands away from the outer wall such that the snap fixture element is configured to receive a lip extending away from the outer wall.

19. The male connector part of claim 17, wherein the male body part is a rigid or semi-rigid structure.

20. The male connector part of claim 17, wherein the male body part includes a sealing surface which provides a secondary seal surface.

* * * * *